(12) United States Patent
Celli

(10) Patent No.: US 6,319,463 B1
(45) Date of Patent: Nov. 20, 2001

(54) EQUIPMENT FOR STERLIZING SOILS

(75) Inventor: Alfredo Celli, Forli'(IT)

(73) Assignee: ALCE Garden S.r.l. (IT)

( * ) Notice: Subject to any disclaimer, the term of this patent is extended or adjusted under 35 U.S.C. 154(b) by 0 days.

(21) Appl. No.: 09/696,805

(22) Filed: Oct. 25, 2000

Related U.S. Application Data

(62) Division of application No. 09/031,852, filed on Feb. 27, 1998.

(51) Int. Cl.[7] .................................................. A61L 2/08
(52) U.S. Cl. ............................. 422/26; 422/26; 422/28; 422/29; 422/32; 422/292; 422/295; 47/1.42; 47/DIG. 10; 111/118; 111/127
(58) Field of Search .................................. 422/26, 28, 29, 422/32, 292, 295; 47/1.42, DIG. 10; 111/118, 127

(56) References Cited

U.S. PATENT DOCUMENTS

| | | | |
|---|---|---|---|
| 3,714,913 | * | 2/1973 | Gandrud ........................ 47/DIG. 10 |
| 3,854,241 | * | 12/1974 | Zimmermann et al. ........ 47/DIG. 10 |
| 4,010,900 | * | 3/1977 | Flix et al. ...................... 47/DIG. 10 |
| 4,337,078 | * | 6/1982 | Petrov et al. ................... 47/DIG. 10 |
| 4,409,910 | * | 10/1983 | Hoyle et al. ................... 47/DIG. 10 |
| 4,481,894 | * | 11/1984 | Brenn ................................ 111/127 |
| 4,927,293 | * | 5/1990 | Campbell ....................... 47/DIG. 10 |
| 4,951,417 | * | 8/1990 | Gerken et al. ................. 47/DIG. 10 |
| 5,033,397 | * | 7/1991 | Colburn, Jr. ................... 47/DIG. 10 |
| 5,323,720 | * | 6/1994 | Moore, Jr. ..................... 47/DIG. 10 |
| 5,406,747 | | 4/1995 | Kiefl ..................................... 47/1.42 |
| 5,553,414 | | 9/1996 | Chapman et al. ................... 47/1.42 |
| 5,568,895 | | 10/1996 | Webb et al. ........................... 241/16 |
| 5,622,123 | * | 4/1997 | Rajamannan ........................ 111/118 |
| 5,730,074 | * | 3/1998 | Peter .................................... 111/118 |
| 6,183,532 | * | 2/2001 | Celli ..................................... 47/1.01 |

* cited by examiner

*Primary Examiner*—Robert J. Warden, Sr.
*Assistant Examiner*—Imad Soubra
(74) *Attorney, Agent, or Firm*—Orum & Roth

(57) ABSTRACT

The present invention relates to a method for sterilizing soils and of the equipment related thereto. The method comprises sequentially at least the following phases:—dispersion into the soil of at least one compound, solid, liquid or gaseous, able to react exothermically with water and/or steam, or other substance;—injection of at least one jet of water and/or steam, or of another substance, into the soil in such a way as to produce heat in the subsequent reaction with the compound. Between the two aforesaid phases it is convenient to proceed to break up the soil to favor its mixing, with the compound and create the best conditions for the reaction. The equipment suitable to carry out this method comprise autonomous locomotion means to be able to reach the open countryside, a tank to transport water or another suitable substance and a related appendage to convey it into the soil, a second tank for the compound that is to react exothermically, with water and/or steam, or, in general, with the substance transported in the first tank, and means for dispersing the compound into the soil. It can also be provided with a boiler to heat or vaporize the reactant contained in the tank, as well as an agricultural tool to favor the mixing, of the compound, the penetration of the reactant into the soil and the subsequent reaction thereof. (FIG. 1)

14 Claims, 1 Drawing Sheet

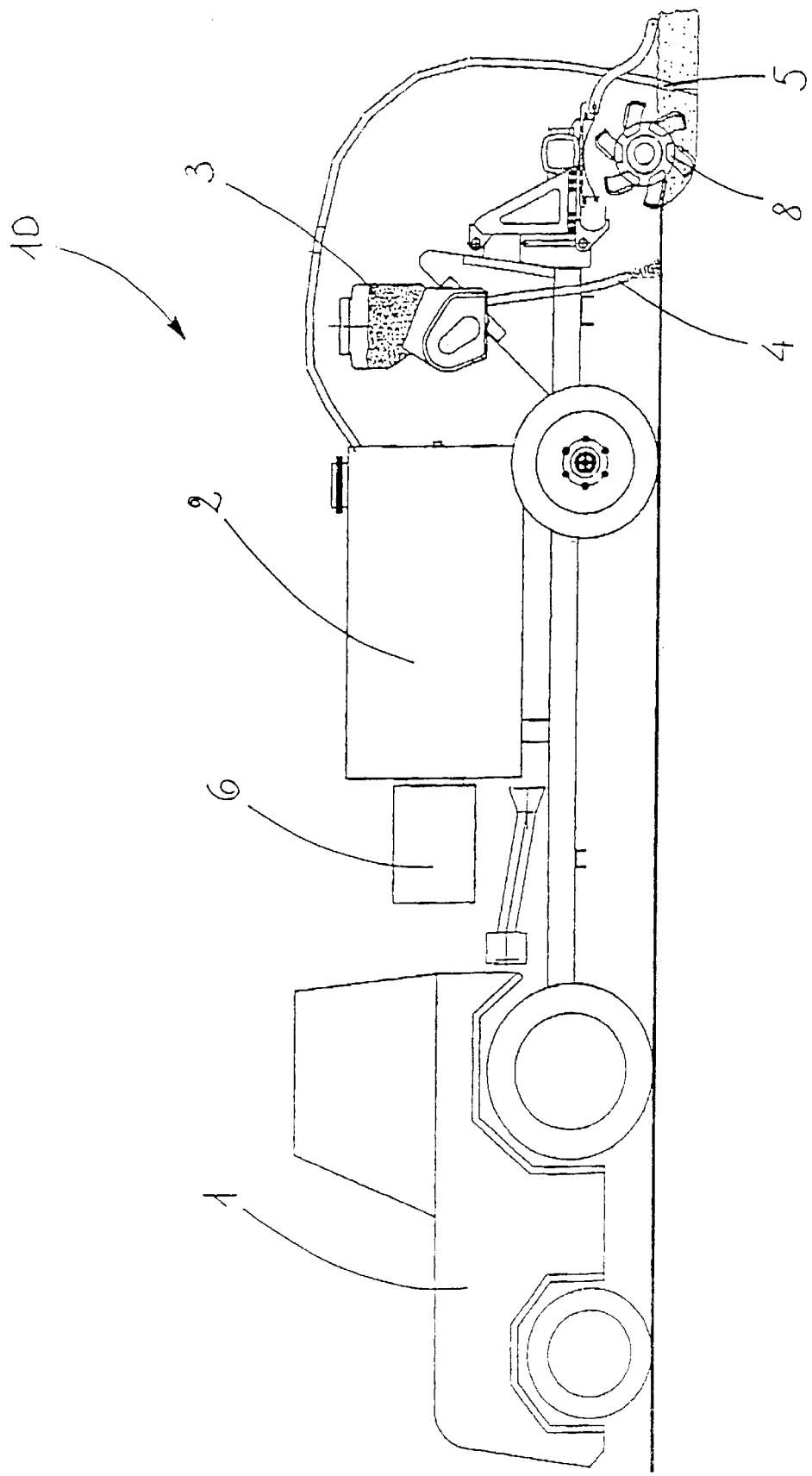

EQUIPMENT FOR STERILIZING SOILS

This application is a Divisional of Ser. No. 09/031,852 filed Feb. 27, 1998.

BACKGROUND OF THE DISCLOSURE

The present invention relates to a method for sterilizing soils and to the equipment related thereto.

The grooving specialization in crops and the so-called single-crop systems, particularly widespread in the sector of ornamental plants, garden vegetables, corn and beet, generate a strong interaction between the microflora of the soil and the radical system of the plants.

Moreover, numerous vegetable and animal parasites can survive in the soil even for many years, until they come in contact with plants prone to suffer from their pathogenetic action.

The continued cultivation of such plants in the same soil thus leads to ailments in their growth and to a progressive deterioration in harvest yields. The first and most ancient way to obviate this problem consists of the so-called "crop rotation" or, more generally, of prolonging the interval during which a crop remains absent from a soil. In this situation, the soil dwelling parasites of the plant itself progressively die due to "starving".

However, there are cases wherein the "rotation" method does not provide sufficient reliability many parasites are able to survive as parasites of other plants or remaining in a state of quiescent life; other times, abandoning a certain crop for a given period may not be economically advantageous. It is then necessary to resort to rather energetic interventions, which must therefore be applied only on the bare soil, some time before planting a new crop. These are rather onerous processes that accomplish the disinfection or disinfestation by means of chemical or physical interventions.

Chemical interventions consist of the administration of fungicides, insecticides, plant protection products or fumigation products: such intervention are long, very costly and highly hazardous for environmental pollution. After their execution, rather long time intervals are required before it is possible to proceed with the cultivation of the treated soil.

Physical interventions essentially consist of administering heat to the soil, heat which can be produced and distributed in various ways. As a rule, regardless of the methods used, heating the soil up to 80–90° C. is sufficient to kill all parasites present. This type of operation allows to start cultivation a short time afterwards, as soon as the temperature of the soil drops to 25–30° C.

Among physical interventions, treatments with dry heat, performed by heating the soil in the so-called country ovens, are the least effective ones, both because the results they yield are not always satisfactory, and because in any case they can only be applied to small plots of land.

Sterilization with boiling water entails prohibitive expenses and it is only plausible for very small plots of land.

Steam treatment finds applications for soil disinfection in greenhouses, stable seed-beds or small open plots: it can be accomplished both introducing the soil into large cement tanks, or in other containers, then passing through the soil both the steam produced by a generator and fixed or movable tools positioned on or within the soil to be disinfected.

In this latter case, the steam, produced by an appropriate generator, moves through pipes which lead it to the aforesaid dispensing tools of various designs. Use is made of hood dispensers, similar to upside down cases or to canvas sheets with the edges stuck in the soil, wherein the steam is inserted, or even comb dispensers, comprising a horizontal pipe wherefrom a series of vertical pipes depart which convey the steam into the soil. Hood dispensers are particularly indicated when the sterilization has to reach depths in the order of 20–25 cm, comb dispensers for greater depths. Lastly it is possible to use large self-propelled machines, able to intervene autonomously.

Only sufficiently profitable cultivations, for instance floriculture, justify the use of this system which presents, for wide open spaces, logistically insurmountable difficulties.

SUMMARY OF THE INVENTION

The object of the present invention is to provide a method for sterilizing soils, and equipment related thereto, eliminating the drawbacks mentioned above.

The invention, as it is characterized by the claims, solves the problem of making soil sterilization practically feasible also in wide open spaces, for instance in the country, exploiting, known chemical reactions of the exothermic type.

One of the advantages obtained through the present invention consists essentially of the fact that energy consumption for steam production, or for water heating, is drastically reduced. Consequently, lighter machines can be used which, on one hand, contribute further to reduce consumption, on the other hand make it easier to carry out the sterilization in the open country.

Another important advantage consists of the fact that, to perform the exothermic reaction, it is possible to employ substances which are beneficial to the soil also from other viewpoints, for instance to redress its pH balance or to fertilize it.

The result of the exothermic reaction could even be in turn a substance acting as a fertilizer for the soil thus to be treated.

BRIEF DESCRIPTION OF THE DRAWING

The invention is described in more detail hereafter with the aid of the drawing which shows an embodiment provided purely by way of non limiting example, a schematic side view of the equipment

DESCRIPTION OF THE PREFERRED EMBODIMENTS

As can be observed in the FIGURE, the equipment (10) comprises autonomous means of locomotion (1), a tank (2) for transporting a reactant, for instance water, and at least one appendage (5) to convey such reactant into the soil. Since for displacements in the open country the equipment (10) described must be able to move freely, the aforesaid means of locomotion (1) can consist of a tractor or of an engine integral to the chassis of the equipment (10) itself.

In order to produce an exothermic reaction within the soil, the equipment (10) further comprises a second tank (3) for a compound that is to react exothermically with water and,or steam, or with any other suitable substance, and means (4) for dispensing said compound into the soil.

Since the heat produced by the chemical reaction is affected by the compound used, and the latter may vary according to other requirements, soil sterilization, i.e. the suppression of the parasites, will be obtained by injecting water or another substance at an optimal temperature to be assessed on a case by case basis. Therefore, it may be necessary to heat the water or even to vaporize it before injecting it into the soil. To this end, the equipment (10) can comprise a boiler (6), able to vaporize the water to be injected into the soil or, more in general, to raise the temperature of the reactant.

Since it is certainly desirable to create the best conditions for a uniform sterilization of the soil, the latter could be broken up beforehand with a mechanical hoe or a harrow. The optimal solution however consists of providing the equipment (10) in question with an agricultural tool (8) such as the aforesaid ones, interposed between the means (4) for dispensing the compound which is to react exothermically with the reactant contained in the first tank (2) and the appendage (5) to convey such reactant into the soil, so as to disperse the compound into the soil and favor the penetration therein of water and/or steam, or, in general, of the substance used.

The equipment (10) described above is functional to carry out a method to sterilize soils, also new and original, which could be carried out also with other machinery while still maintaining its innovative characteriztics. Such method comprises sequentially at least the following phases:

dispersing into the soil at least one compound able to react exothermically with water and/or steam, or other suitable substance;

injecting at least one jet of water and/or steam into the soil, or of another substance, in order to obtain an exothermic reaction with the compound previously dispersed therein.

As has been mentioned above, it is convenient for the method to comprise, between the dispersion of the compound and the injection of water and/or steam, or of any other substance, an intermediate phase consisting of breaking up the soil, in order to favor the dispersion of the compound and to create the best conditions for the exothermic reaction to take place.

The compound, usable in solid, liquid or gaseous form, could advantageously be constituted by a fertilizer or a supplementer, i.e. by a substance that is also able to re-balance the nature of the soil, towards a greater acidity or a greater alkalinity, depending on the crops to be planted.

Purely by way of example, one could use quicklime (CaO), caustic soda (NaOH) and caustic potash (KOH) for acid soils or orthophosphoric acid ($H_3PO_4$) for alkaline soils. While the former give rise with water ($H_2O$) to strongly exothermic reactions, wherein hydroxyl ions ($OH^-$) are freed which raise the pH value, orthophosphoric acid reacts exothermically with water producing hydrogen ions ($H^+$) which reduce the pH value. In all examples mentioned above, moreover, essential substances for the development of the crops are released in ionic forms, respectively calcium, sodium, potassium and phosphorus.

Alternatively, to heat the soil, exothermic reactions could be provoked using materials with porous microstructure or natural or synthetic zeolites.

To these substances could be added a neutral substance, such as a fertilizer of natural origin rich in organic substances and in micro-organisms useful to the plants, particular well suited for restoring the bacterial microflora, for the most part eliminated by the heat produced in the course of the sterilization.

The invention thus conceived can be subject to numerous modifications and variations, without thereby departing, from the scope of the inventive concept. Moreover, all components may be replaced with technically equivalent elements.

In practice, modifications and/or improvements are obviously, possible without thereby departing from the scope of the following claims.

What is claimed is:

1. Equipment for sterilizing soil, comprising:
 a first tank for transporting a first reactant;
 at least one appendage leading from said first tank for dispersing said first reactant into soil;
 a second tank for transporting a second reactant which is able to react exothermically with said first reactant;
 means for dispensing said second reactant from said second tank into contact with said soil; and
 movable means for supporting said first tank and said second tank.

2. Equipment according to claim 1, further comprising a boiler to raise the temperature or vaporize said second reactant which is injected into said soil.

3. Equipment according to claim 1, further comprising a tool for breaking up said soil, said tool located between said movable means and said at least one appendage in order to disburse said second reactant into said soil.

4. Equipment for sterilizing soil, comprising:
 a tank for a reactant
 a movable means supporting said tank for transporting said reactant,
 a second tank for a compound which reacts exothermically with said reactant,
 a means for dispensing said compound in contact with the soil, and
 an appendage to convey the reactant into the soil where the compound has been dispensed to provide an exothermal reaction within the soil to sterilize the same soil.

5. Equipment according to claim 4, wherein it comprises a boiler able to raise the temperature of the reactant to be injected into the soil or to vaporize it.

6. Equipment according to claim 4, wherein it comprises a soil breaking up tool, interposed between said means for dispensing the compound and the appendage for conveying the reactant into the soil, in such a way as to disperse the compound into the soil and favor a uniform exothermal reaction within the soil with the subsequently injected reactant.

7. Equipment according to claim 4, wherein the reactant is water and/or steam.

8. Equipment according to claim 4, wherein the compound is in solid, liquid or gaseous state.

9. Equipment according to claim 4, wherein said compound comprises at least a natural or synthetic zeolite.

10. Equipment according to claim 4, wherein the reactant is provided by injection of at least one jet of water, hot water or steam into the soil, in order to obtain an exothermic reaction with the compound previously dispersed therein.

11. Equipment according to claim 4, wherein one of said reactant is chosen from the group comprising quicklime (CaO), caustic soda (Na OH) and caustic potash (KOH).

12. Equipment according to claim 4, wherein one of said reactant is orthophosphoric acid ($H_3PO_4$).

13. Equipment for sterilizing soil, comprising:
 a movable means supporting
 a tank for a reactant,
 a second tank for a compound which reacts exothermically with said reactant,
 a means for dispensing said compound in contact with the soil,
 at least one appendage to convey the reactant into the soil where the compound has been dispensed to provide an exothermal reaction within the soil to sterilize the same soil, and a boiler able to raise the temperature of the reactant to be injected into the soil or to vaporize it.

14. Equipment for sterilizing soil, comprising:

a movable means supporting
- a tank for transporting a reactant,
- a second tank for a compound which reacts exothermically with said reactant,
- a means for dispensing said compound in contact with the soil,
- at least one appendage to convey the reactant into the soil, and
- a soil breaking up tool, interposed between said means for dispensing the compound, which reacts exothermically with the reactant contained in the first tank, and the appendage for conveying the reactant into the soil, to disperse said compound into the soil, and said appendage for conveying said reactant where the compound has been dispersed to obtain a uniform exothermal reaction within the soil.

* * * * *